(12) United States Patent
Diner et al.

(10) Patent No.: US 8,460,898 B2
(45) Date of Patent: Jun. 11, 2013

(54) ORGANIC SOLVENT PRETREATMENT OF BIOMASS TO ENHANCE ENZYMATIC SACCHARIFICATION

(75) Inventors: Bruce A Diner, Chadds Ford, PA (US); Janine Fan, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/539,696

(22) Filed: Jul. 2, 2012

(65) Prior Publication Data

US 2012/0270269 A1 Oct. 25, 2012

Related U.S. Application Data

(62) Division of application No. 12/639,059, filed on Dec. 16, 2009, now Pat. No. 8,241,873.

(60) Provisional application No. 61/139,179, filed on Dec. 19, 2008.

(51) Int. Cl.
| | |
|---|---|
| *C12P 19/00* | (2006.01) |
| *C12P 13/04* | (2006.01) |
| *C12P 7/40* | (2006.01) |
| *C12P 7/02* | (2006.01) |
| *C12P 7/04* | (2006.01) |
| *C12P 7/16* | (2006.01) |
| *C12P 7/06* | (2006.01) |
| *C12P 7/08* | (2006.01) |
| *C07H 1/06* | (2006.01) |

(52) U.S. Cl.
USPC ............ 435/72; 435/106; 435/136; 435/155; 435/157; 435/160; 435/161; 435/163; 536/128

(58) Field of Classification Search
USPC ............ 435/72, 106, 136, 155, 157, 16, 161, 435/163; 536/128
See application file for complete search history.

(56) References Cited

U.S. PATENT DOCUMENTS

| | | | |
|---|---|---|---|
| 1,817,525 | A | 8/1931 | Richter |
| 1,891,337 | A | 12/1932 | Seaman |
| 3,033,695 | A | 5/1962 | Glab |
| 3,490,991 | A | 1/1970 | Fisher et al. |
| 3,490,993 | A | 1/1970 | Fisher et al. |
| 4,329,200 | A | 5/1982 | Sarkanen |
| 4,470,851 | A | 9/1984 | Paszner et al. |
| 4,597,830 | A | 7/1986 | April et al. |
| 5,171,592 | A | 12/1992 | Holtzapple et al. |
| 6,555,350 | B2 | 4/2003 | Ahring et al. |
| 2007/0029252 | A1 | 2/2007 | Dunson, Jr. et al. |
| 2007/0031919 | A1 | 2/2007 | Dunson, Jr. et al. |
| 2007/0178569 | A1 | 8/2007 | Leschine et al. |
| 2010/0159517 | A1 | 6/2010 | Diner et al. |
| 2010/0159518 | A1 | 6/2010 | Diner et al. |
| 2010/0178677 | A1 | 7/2010 | Dunson, Jr. et al. |

FOREIGN PATENT DOCUMENTS

| | | |
|---|---|---|
| GB | 925524 A | 5/1963 |
| GB | 1294072 A | 10/1972 |

OTHER PUBLICATIONS

Kleinert, Theodor N., Organosolv pulping with aqueous alcohol, Tappi, Aug. 1974, pp. 99-102, vol. 57, No. 8.

Park, Jung-Keug et al., Ammonia Catalyzed Organosolv Delignification of Poplar, Chemical Engineering Communications, 1988, pp. 187-205, vol. 65.

Lee, Yong-Hyun et al., Evaluation of Organosolv Processes for the Fractionation and Modification of Corn Stover for Bioconversion, Biotechnology and Bioengineering, 1987, pp. 572-581, vol. 29, John Wiley & Sons, Inc.

Peter, Siegfried et al., Degradation of Lignin with Monomethylamine, Chemical Engineering Technology, 1992, pp. 213-217, vol. 15.

*Primary Examiner* — Herbert J Lilling

(57) ABSTRACT

Biomass is pretreated using an organic solvent solution under alkaline conditions in the presence of ammonia and optionally an additional nucleophile to fragment and extract lignin without loss of hemicellulose. Pretreated biomass is further hydrolyzed with a saccharification enzyme consortium. Fermentable sugars released by saccharification may be utilized for the production of target chemicals by fermentation.

19 Claims, No Drawings

US 8,460,898 B2

ORGANIC SOLVENT PRETREATMENT OF BIOMASS TO ENHANCE ENZYMATIC SACCHARIFICATION

This application is a divisional of U.S. Ser. No. 12/639059, filed Dec. 16, 2009, now which claims the benefit of U.S. Provisional Application No. 61/139,179, filed Dec. 19, 2008, the disclosure of which is hereby incorporated in its entirety.

FIELD OF THE INVENTION

Methods for producing readily saccharifiable carbohydrate-enriched lignocellulosic biomass are provided and disclosed. Specifically, pretreated biomass is prepared through simultaneous fragmentation and selective extraction of lignin in an organic solvent solution in the presence of low to moderate concentrations of ammonia and one or more nucleophile at elevated temperatures under alkaline conditions. The remaining carbohydrate-enriched solids in the pretreated biomass may then be subjected to enzymatic saccharification to obtain fermentable sugars, which may be subjected to further processing for the production of target products.

BACKGROUND OF THE INVENTION

Cellulosic and lignocellulosic feedstocks and wastes, such as agricultural residues, wood, forestry wastes, sludge from paper manufacture, and municipal and industrial solid wastes, provide a potentially large renewable feedstock for the production of chemicals, plastics, fuels and feeds. Cellulosic and lignocellulosic feedstocks and wastes, composed of cellulose, hemicellulose, pectins and of lignin are generally treated by a variety of chemical, mechanical and enzymatic means to release primarily hexose and pentose sugars, which can then be fermented to useful products.

Pretreatment methods are often used to make the polysaccharides of lignocellulosic biomass more readily accessible to cellulolytic enzymes. One of the major impediments to cellulolytic enzyme digest is the presence of lignin, a barrier that limits the access of the enzymes to their substrates, and a surface to which the enzymes bind non-productively. Because of the significant costs associated with enzymatic saccharification, it is desirable to minimize the enzyme loading by either inactivation of the lignin to enzyme adsorption or its outright extraction.

Another challenge is the inaccessibility of the cellulose to enzymatic hydrolysis either because of its protection by hemicellulose and lignin or by its crystallinity. Pretreatment methods that attempt to overcome these challenges include: steam explosion, hot water, dilute acid, ammonia fiber explosion, alkaline hydrolysis (including ammonia recycled percolation), oxidative delignification and organosolv.

Organosolv methods, as previously practiced for the treatment of lignocellulose biomass, for either the production of pulp or for biofuels applications, while generally successful in lignin removal, have suffered from poor sugar recoveries, particularly of xylose. For example, the use of slightly acidic ethanol-water mixtures (e.g., EtOH 42 weight %) at elevated temperature to remove lignin from lignocellulosic biomass (Kleinert, T. N., Tappi 57: 99-102, 1974) resulted in substantial loss of carbohydrate. Dilute acid hydrolysis at 95° C. followed by organic solvent extraction and enzymatic saccharification (Lee, Y-H. et al., Biotech. Bioeng., 29: 572-581, 1987) resulted in substantial loss of hemicellulose during hydrolysis, additional carbohydrate loss upon organic solvent extraction and poor yield (~50% of total carbohydrate) upon enzymatic saccharification of residue.

Treatment of biomass with gaseous water and methylamine followed by extraction with organic solvent and then extraction with water, required three steps and resulted in a substantial loss of carbohydrate (Siegfried, P. and Götz, R., Chem. Eng. Technol., 15: 213-217, 1992). Treatment with polyamines or ethylamine in water-aliphatic alcohol mixtures plus catalyst at elevated temperature required high liquid/solids ratio and low concentrations of alcohol led to poor sugar recovery, particularly of xylan (U.S. Pat. No. 4,597,830A). Thioglycolate in aqueous alkaline solution used to treat lignocellulosic biomass at elevated temperature, followed by a hot water wash required use of alkali-metal or alkaline-earth hydroxides. This method requires the costly disposal of inorganic ions, high weight % thioglycolate, and use of large volumes of water (U.S. Pat. No. 3,490,993). Treatment with organic solvent-water mixtures in the presence of sulfide/bisulfide at elevated temperatures required a high solvent/solids ratio and elevated sulfur content and resulted in a substantial loss of carbohydrate, (U.S. Pat. No. 4,329,200A).

The use of aqueous organic solvent containing high concentrations of ammonia at elevated temperatures to treat lignocellulosic biomass (Park J.-K. and Phillips, J. A., Chem. Eng. Comm., 65: 187-205, 1988) required the use of a high liquid to solids ratio in pretreatment and resulted in substantial loss of hemicellulose and poor enzymatic saccharification of cellulose.

Additional shortcomings of previously applied methods include, separate hexose and pentose streams (e.g., dilute acid), inadequate lignin extraction or lack of separation of extracted lignin from polysaccharide, particularly in those feedstocks with high lignin content (e.g., sugar cane bagasse, softwoods), disposal of waste products (e.g., salts formed upon neutralization of acid or base), and poor recoveries of carbohydrate due to breakdown or loss in wash steps. Other problems include the high cost of energy, capital equipment, and pretreatment catalyst recovery, and incompatibility with saccharification enzymes.

One of the major challenges of biomass pretreatment is to maximize the extraction or chemical neutralization (with respect to non-productive binding of cellulolytic enzymes) of the lignin while minimizing the loss of carbohydrate (cellulose plus hemicellulose) via low-cost efficient processes. The higher the selectivity, the higher the overall yield of monomeric sugars following combined pretreatment and enzymatic saccharification.

There is therefore a need to develop a single step process using substantially lower liquid to solid ratio in pretreatment and recyclable base without substantial loss of hemicellulose and poor enzymatic saccharification of cellulose. The current disclosure addresses this need. In this disclosure, low to moderate concentrations of ammonia in the presence of one or more nucleophiles is used for an organic solvent solution-mediated fragmentation and selective extraction of lignin at elevated temperatures under alkaline conditions. This cost-effective process maintains the hemicellulose content of the biomass while selectively removing lignin and produces carbohydrate-enriched biomass that is highly susceptible to enzymatic saccharification. The pretreated biomass produced by the processes described herein results in very high yields of fermentable sugars (glucose, as well as xylose) following saccharification and in turn, high yields of target products (e.g., value-added chemicals and fuels) after fermentation. Surprisingly, use of low to moderate concentrations of ammonia and in the presence of one or more nucleophile resulted in significantly improved lignin fragmentation and extraction and high carbohydrate retention, particularly with respect to hemicellulose.

SUMMARY OF THE INVENTION

The present invention provides a method for producing readily saccharifiable carbohydrate-enriched biomass and for selectively extracting lignin from lignocellulosic biomass while nearly quantitatively retaining carbohydrates, particularly hemicellulose. The methods include treating lignocellulosic biomass with an organic solvent solution comprising low to moderate concentrations of ammonia and one or more nucleophile(s) under alkaline conditions at elevated temperatures. Following pretreatment, the biomass may be further treated with a saccharification enzyme consortium to produce fermentable sugars. These sugars may be subjected to further processing for the production of target products.

Accordingly the invention provides a method for producing carbohydrate-enriched biomass with high retention of hemicellulose comprising:
(a) providing lignocellulosic biomass comprising lignin, cellulose and hemicellulose;
(b) suspending the biomass of (a) in an organic solvent solution comprising water, ammonia in an amount of about 2% to about 20% relative to weight of dry biomass and one or more nucleophile, whereby a biomass-solvent suspension is formed under alkaline conditions;
(c) heating the biomass-solvent suspension to a temperature of about 100-220° C. for about 5 minutes to about 5 hours whereby lignin is fragmented and is dissolved in the suspension; and
(d) filtering free liquid under pressure after heating the suspension in (c) whereby the dissolved lignin is removed and whereby carbohydrate-enriched biomass with high retention of hemicellulose is produced.

In another embodiment the invention provides A method of simultaneous fragmentation and selective extraction of lignin from lignocellulosic biomass to produce a substantially lignin-free biomass comprising:
(a) providing:
1) an amount of lignocellulosic biomass comprising ligning and carbohydrate;
2) a multi-component solvent solution comprising from about 40% to about 70% ethanol in water;
3) ammonia in an amount of 2% to about 20%
4) and one or more nucleophile(s);
(b) contacting said biomass with the multi-component solvent solution of (a) to form a solvent-biomass mixture;
(c) placing the solvent-biomass mixture in a sealed pressure vessel whereby the mixture of (b) is heated at a temperature of about 100° C. to about 220° C. for about 5 minutes to about 5 hours whereby lignin is fragmented and dissolved in the solvent;
(d) removing the dissolved lignin of (c) by filtration; and
(e) washing the residual with organic solvent, whereby substantially lignin-free biomass is produced.

The resulting biomass has a carbohydrate content that is highly-conserved, for example, the carbohydrate content may be greater than or equal to 85% of the biomass carbohydrate as compared to the biomass prior to pretreating as described herein. More specifically, the resulting biomass is carbohydrate-enriched such that at least about 50%, 55%, 60%, 65%, 70%, 75%, 80%, 85%, 90%, 95%, 98%, or 100% of carbohydrate is retained following pretreatment as compared to the amount of carbohydrate present in the biomass before pretreating as described herein. Further, the resulting hemicellulose content is retained such that at least about 50%, 55%, 60%, 65%, 70%, 75%, 80%, 85%, 90%, 95%, 98%, or 100% of hemicellulose is retained following pretreatment as compared to the amount of hemicellulose present in the biomass before pretreating as described herein.

Particularly suitable feedstocks for use in the methods of the invention include but are not limited to switchgrass, waste paper, sludge from paper manufacture, corn fiber, corn cobs, corn husks, corn stover, grasses, wheat, wheat straw, hay, barley, barley straw, rice straw, sugar cane bagasse, sugar cane straw, yellow poplar, sorghum, soy, components obtained from processing of grains, trees, branches, roots, leaves, wood chips, sawdust, shrubs and bushes, vegetables, fruits, flowers, animal manure and combinations thereof.

DETAILED DESCRIPTION OF THE INVENTION

Applicants specifically incorporate the entire content of all cited references in this disclosure. Unless stated otherwise, all percentages, parts, ratios, etc., are by weight. Trademarks are shown in upper case. Further, when an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides a process for the treatment of biomass in order to produce readily saccharifiable carbohydrate-enriched biomass to enhance the subsequent enzymatic saccharification step. A process involving a pretreatment step wherein lignin is simultaneously fragmented and extracted using an organic solvent under alkaline conditions at elevated temperatures in the presence of ammonia is employed. Additional nucleophiles may be employed for further benefit. The treated biomass is then filtered and washed to remove solubilized lignin, acetic acid, acetamides, alkylamides and excess reagent and then digested with a saccharification enzyme consortium to produce fermentable sugars. The sugars may then be further processed to one or more target product. The removed lignin may also be further processed and utilized for other purposes (such as burning for energy) to increase efficiency.

Definitions

The following definitions are used in this disclosure:

"Room temperature" and "ambient" when used in reference to temperature refer to any temperature from about 15° C. to about 25° C.

"Fermentable sugars" refers to a sugar content primarily comprising monosaccharides and some disaccharides (that can be used as a carbon source by a microorganism (some polysaccharides may be present)) in a fermentation process to produce a target product. "Readily fermentable sugars" means that additional costly processing is not necessary and/ or that a fermentative microorganism can be contacted with the resulting sugars with minimal impediments from inhibitors or other components that may adversely affect fermentation.

"Lignocellulosic" refers to material comprising both lignin and cellulose. Lignocellulosic material may also comprise hemicellulose. In the processes described herein, lignin is dissolved and substantially removed from the lignocellulosic biomass to produce a carbohydrate-enriched biomass.

"Hemicellulose" refers to heteropolymeric branched chain carbohydrate that is present in almost all plant cell walls along with cellulose. It is comprised primarily of pentose sugars, mostly xylose, but also by arabinose, through which it is frequently esterified to lignin. It can also contain six-carbon uronic acids and some hexose sugars, glucose, galactose, mannose and rhamnose. Hemicellulose has a random, amorphous structure with little strength and is easily hydrolyzed by dilute acid or base and hemicellulase enzymes.

"High retention of hemicellulose" as used herein refers to retention of ≧85% of hemicellulose present in the starting material.

"Dissolved lignin" as referred to herein means the lignin that is dissolved in an organic solvent solution.

"AI lignin" refers to acid-insoluble lignin.

"Autohydrolysis" refers to the hydrolysis of biomass in the presence of solvent (water or organic solvent plus water) plus heat with no further additions, such as without exogenous acid or base or hydrolytic enzyme addition.

"Cellulosic" refers to a composition comprising cellulose.

"Target product" refers to a chemical, fuel, or chemical building block produced by fermentation. Product is used in a broad sense and includes molecules such as proteins, including, for example, peptides, enzymes and antibodies. Also contemplated within the definition of target product are ethanol and butanol.

"Dry weight of biomass" refers to the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

"Selective extraction" means removal of lignin while substantially retaining carbohydrates.

A "solvent solution" and "an organic solvent solution" as used herein is an organic solvent mixture in water that includes any organic liquid that dissolves a solid, liquid, or gaseous solute, resulting in a solution. The most suitable solvent solutions for this invention are organic solvents such as ethanol, methanol, n-propanol, isopropanol, n-butanol, 2-butanol, isobutanol, t-butanol, pentanol and hexanol and diols with the same number of carbons. They can also include aprotic solvents. The solvent solutions can include additional components in mixture with the solution, e.g, the solvent solution may include one or more nucleophile.

"Biomass" and "lignocellulosic biomass" as used herein refer to any lignocellulosic material, including cellulosic and hemi-cellulosic material, for example, bioenergy crops, agricultural residues, municipal solid waste, industrial solid waste, yard waste, wood, forestry waste and combinations thereof, and as further described below. Biomass has a carbohydrate content that comprises polysaccharides and oligosaccharides and may also comprise additional components, such as protein and/or lipid.

"Highly conserved" as used herein refers to the carbohydrate content of the lignocellulosic material after the processing steps described herein. In an embodiment of the invention, the highly conserved carbohydrate content provides for sugar yields after saccharification that are substantially similar to theoretical yields with minimal loss of sugar yield from the processes described herein. In an embodiment of the invention, highly conserved with reference to carbohydrate content refers to the conservation of greater than or equal to 85% of the biomass carbohydrate as compared to biomass prior to pretreating as described herein.

"Preprocessing" as used herein refers to processing of lignocellulosic biomass prior to pretreatment. Preprocessing is any treatment of biomass that prepares the biomass for pretreatment, such as mechanically milling and/or drying to the appropriate moisture contact.

"Biomass-solvent suspension" refers to a mixture of biomass and solvent. The biomass-solvent solution may comprise additional components such as one or more alkylamine, ammonia, sulfide reagents, etc.

"Saccharification" refers to the production of fermentable sugars from primarily polysaccharides by the action of hydrolytic enzymes. Production of fermentable sugars from pretreated biomass occurs by enzymatic saccharification by the action of cellulolytic and hemicellulolytic enzymes.

"Pretreating biomass" or "biomass pretreatment" as used herein refers to subjecting native or preprocessed biomass to chemical or physical action, or any combination thereof, rendering the biomass more susceptible to enzymatic saccharification or other means of hydrolysis prior to saccharification. For example, the methods claimed herein may be referred to as pretreatment processes that contribute to rendering biomass more accessible to hydrolytic enzymes for saccharification.

"Pretreatment filtrate" means the free liquid that is in contact with the biomass following pretreatment and which is separated by filtration.

"Pretreated Biomass" as used herein refers to native or preprocessed biomass that has been subjected to chemical or physical action, or any combination thereof, rendering the biomass more susceptible to enzymatic saccharification or other means of hydrolysis prior to saccharification.

"Air-drying the filtered biomass" can be performed by allowing the biomass to dry through equilibration with the air of the ambient atmosphere.

"Readily saccharifiable biomass" means biomass that is carbohydrate-enriched and made more amenable to hydrolysis by cellulolytic or hemi-cellulolytic enzymes for producing monomeric and oligomeric sugars, i.e., pretreated biomass as described herein.

"Carbohydrate-enriched" as used herein refers to the biomass produced by the process treatments described herein. In one embodiment the readily saccharifiable carbohydrate-enriched biomass produced by the processes described herein has a carbohydrate concentration of greater than or equal to 85% of the dried biomass by weight, while having removed 75% or greater of the starting biomass lignin content based on dry weight.

"Heating the biomass suspension" means subjecting the biomass suspended in a solvent to a temperature greater than ambient or room temperature. Temperatures relevant to the present pretreatments are from about 100 to about 220° C., or from about 140 to about 180° C., or any temperature within or approximately these ranges.

"Filtering free liquid under pressure" means removal of unbound liquid through filtration, with some pressure difference on opposite faces of the filter.

"Alkaline" or "under alkaline conditions" means a pH of greater than 7.0. In the present invention, "under alkaline conditions", also means a pH of the biomass-solvent suspension equal to or greater than the pKas of the nucleophiles present such that these are substantially deprotonated and more highly reactive than in their protonated states. These nucleophiles would include alkylamines, and ammonia, thiols, polysulfides and hydrosulfide (if present).

"Divalent alkane" means a linear, branched or cyclic alkane with two open valences.

"Carbohydrate content" means the percent of the dry matter of a lignocellulosic biomass sample that is attributable to glucan, xylan and arabinan and includes carbohydrate from cellulose and hemicellulose.

"Substantially retaining carbohydrate content" means retention of the maximum amount (e.g., ≦85% of the original content) of each of the glucan, xylan and arabinan, in a pretreatment process applied to lignocellulosic biomass.

"Air-dried sample" means a pretreated sample which has been allowed to air-dry at ambient temperature and pressure to the point where its moisture content is in equilibrium with that of the ambient air, typically ≧85% dry matter.

"Substantially lignin-free biomass" means a pretreated sample in which about ≧75% of the lignin is removed.

"Dry biomass" means biomass with a dry matter content of ≧85%. Methods for drying the biomass include exposure at ambient temperature to vacuum or flowing air at atmospheric pressure and or heating in an oven or a vacuum oven.

"Multi-component solvent" means a solvent containing organic solvent, water, and reagents capable of chemical attack on the lignin.

"Pressure vessel" is a sealed vessel that may be equipped or not with a mechanism for agitation of a biomass/solvent suspension, in which a positive pressure is developed upon heating the lignocellulosic biomass.

"Nucleophile" is a chemical reagent capable of forming a covalent bond with its reaction partner by contributing both of the bonding electrons.

"Hydrolysate" refers to the liquid in contact with the lignocellulose biomass which contains the products of hydrolytic reactions acting upon the biomass (either enzymatic or not), in this case monomeric and oligomeric sugars.

"Organosolv" means a mixture of organic solvent and water which is typically in contact with biomass and in which the lignin or its fragments are soluble.

"Enzyme consortium" or "saccharification enzyme consortium" is a collection of enzymes, usually secreted by a microorganism, which in the present case will typically contain one or more cellulases, xylanases, glycosidases, ligninases and esterases.

"Monomeric sugars" or "simple sugars" consist of a single pentose or hexose unit, e.g., glucose, xylose and arabinose.

"Delignification" is the act of removing lignin from lignocellulosic biomass. In the context of this application, delignification means fragmentation and extraction of lignin from the lignocellulosic biomass with high carbohydrate retention, particularly with respect to hemicellulose, using an organic solvent under alkaline conditions at elevated temperatures in the presence of ammonia and optionally various nucleophiles.

"Fragmentation" is a process in which lignocellulosic biomass is treated with organic solvent under alkaline conditions breaking the lignin down into smaller subunits.

"Selective extraction" is a process by which fragmented lignin is dissolved by treatment with an organic solvent under alkaline conditions leaving behind the polysaccharide.

"Simultaneous fragmentation and selective extraction" as used herein refers to a fragmentation reaction performed in organic solvent such that the lignin fragments go into solution as soon as they are released from the bulk biomass.

Methods for pretreating lignocellulosic biomass to produce readily saccharifiable carbohydrate-enriched biomass, with high retention of hemicellulose, are provided. These methods provide economical processes for rendering components of the lignocellulosic biomass more accessible or more amenable to enzymatic saccharification. The pretreatment can be chemical or physical, or any combination of the foregoing. In this disclosure the pretreatment is performed in the presence of $NH_3$ and optionally an additional base. The presence of an organic solvent and alkaline conditions assists lignin fragmentation and removal and carbohydrate recovery.

In addition, the methods described in the present disclosure minimize the loss of carbohydrate during the pretreatment process and maximize the yield of solubilized (monomeric+oligomeric) sugars in saccharification.

As disclosed above the methods described herein include pretreating lignocellulosic material, with a solvent solution comprising low to moderate concentrations of ammonia and one or more nucleophile as described below, to produce a readily saccharifiable carbohydrate-enriched biomass with high retention of hemicellulose.

Solvents

The methods described herein include use of an organic solvent solution for pretreating biomass and specifically for fragmentation and extraction of lignin. Solvents useful in the present methods are frequently referred to in the art as Organosolv (e.g., E. Muurinen (2000) Organosolv Pulping, A review and distillation study related to peroxyacid pulping Thesis, University of Oulu, pp. 314; S. Aziz, K. Sarkanen, Tappi J., 72/73: 169-175, 1989; A. K. Varsheny and D. Patel, J. Sci. Ind. Res., 47: 315-319, 1988; A. A. Shatalov and H. Pereira, BioResources 1:45-61, 2006; T. N. Kleinert, Tappi J., 57: 99-102, 1979; Practice of organosolv technology for biofuels, derived from Kleinert, which has advanced to the pilot scale using $EtOH/H_2O$ has been described (WO 20071051269), and X. Pan, N. Gilkes, J. Kadla, K. Pye, S. Saka, D. Gregg, K. Ehara, D. Xie, D. Lam, and J. Saddler, Biotechnol. Bioeng., 94: 851-861, 2006. While still at lab scale, use of acetone/$H_2O$ is described in U.S. Pat. No. 4,470,851. Further details on pretreatment technologies related to use of solvents and other pretreatments can be found in Wyman et al., (Bioresource Tech., 96: 1959, 2005); Wyman et al., (Bioresource Tech., 96: 2026, 2005); Hsu, ("Pretreatment of biomass" In Handbook on Bioethanol: Production and Utilization, Wyman, Taylor and Francis Eds., p. 179-212, 1996); and Mosier et al., (Bioresource Tech., 96: 673, 2005). Solvents are used herein for pretreating biomass to remove lignin. Delignification is typically *conducted at temperatures of* 165-225° C., at liquid to biomass ratios of 4:1 to 20:1, at liquid compositions of 50% organic solvent (v/v), and at reaction times between 0.5-12 hours. A number of mono- and polyhydroxy-alcohols have been tested as solvents. Ethanol, butanol and phenol have been used in these reactions (Park, J. K., and Phillips, J. A., Chem. Eng. Comm., 65: 187-205, 1988).

The organosolv or organic solvent solution pretreatment in the present methods may comprise a mixture of water and an organic solvent at selected condition parameters that include temperature, time, pressure, solvent-to-water ratio and solids-to-liquid ratio. The solvent can comprise, but is not limited to, alcohols and aprotic solvents (solvents that do not have a hydrogen atom bound to an oxygen as in a hydroxyl group or a nitrogen as in an amine group, e.g. ketones). The alcohols may include methanol, ethanol, propanol, butanol, pentanol and hexanol and isomers thereof and diols with the same number of carbon atoms, such as 1,2-ethane-diol, 1,2-propandiol, 1,3-propanediol, 1,3-hexanediol.

The concentration of the solvent in solution (i.e. water) in the present invention is from about 2 to about 90% (v/v), or from about 10% to about 85% or from about 20% to about 80% or from about 30% to about 80% or more preferably from about 40% to about 70% (v/v). Specifically, for purposes of an embodiment of the methods herein, EtOH in H$_2$O mixtures from about 0%-80% (v/v) ethanol concentrations were examined and solutions containing 40-70% (v/v) EtOH were found to be most effective.

Ammonia

Ammonia is a low-cost reagent and thus provides an economical means for biomass pretreatment. Ammonia can also be recycled to the pretreatment reactor during pretreatment or following pretreatment, thus enabling an additional economic benefit. Ammonia partitions into a liquid phase and vapor phase and gaseous ammonia can diffuse more easily through biomass than a liquid base, resulting in more efficacious pretreatment at lower concentrations. For example, following pretreatment, as the temperature is decreased to that suitable for saccharification, ammonia gas may be released, optionally in the presence of a vacuum, and may be recycled. In a continuous process, ammonia may be continuously recycled.

In an embodiment, ammonia pretreatment, at low to moderate concentrations, increases carbohydrate recoveries in the biomass. Since NH$_3$ forms an imine with the reducing ends of the polysaccharide chains, it is likely that this reaction inhibits the β-elimination reactions responsible for sugar loss through "peeling" at alkaline pH. NH$_3$ can also drive ammonolysis of lignin which is likely to increase with increasing EtOH concentration by lowering the pKa of NH$_4^+$/NH$_3$ (increasing the NH$_3$/NH$_4^+$ ratio). This reaction may also decrease the formation of quinone methides. The result of low to moderate concentrations of NH$_3$ addition is therefore a further increase in the retention of glucan and xylan under the higher EtOH in H$_2$O pretreatment conditions.

In another embodiment, ammonia (NH$_3$) may be used either alone or in addition to NaOH as an additional component of the solvent solution. The concentration of ammonia used in the present method is minimally a concentration that is sufficient to maintain the pH of the biomass-aqueous ammonia mixture alkaline and maximally less than or equal to about 16 wt %, or about 0%, 2%, 4%, 6%, 8%, 10%, 12%, 14%, 16%, 18% or 20% relative to dry weight of biomass. This low concentration of ammonia is sufficient for pretreatment in accordance with the present methods. Use of a combination of high concentrations of ammonia and organosolv pretreatment for delignification of poplar has been reported (Park, J.-K., and Phillips, J. A., Chem. Eng. Commun., 65, 187-205, 1988). These experiments required application of a high liquid to solids ratio in pretreatment and resulted in substantial loss of hemicellulose and poor enzymatic saccharification of cellulose.

As shown herein in Example 3, ammonia is more effective in the claimed methods when supplemented with low concentrations of NaOH. Using ammonia as the source of alkali, particularly at the low to moderate concentrations disclosed in this application, does not create the disposal problem inherent in the use of NaOH alone, since any unreacted ammonia can be easily recycled.

In addition, the methods described in the present disclosure minimize the loss of carbohydrate during the pretreatment process and maximize the yield of solubilized (monomeric+oligomeric) sugars in saccharification.

As disclosed above the methods described herein include pretreating lignocellulosic material with a solvent solution comprising the components described below to produce a readily saccharifiable carbohydrate-enriched biomass with high retention of hemicellulose.

Additional Components of the Solvent Solution

In an embodiment, NaOH may be employed as an additional component of the solvent solution. NaOH may be used specifically in an EtOH in H$_2$O solvent solution and use of NaOH may include the addition of a catalyst, such as anthraquinone, to the solvent solution for further lignin fragmentation.

The NaOH could be used at various concentrations, such as, in an amount that is at least about from 0.5 to about 20% (w/w biomass). More suitable concentrations include, from about 1 to about 10% (w/w biomass). Most suitable concentrations are between about 2-8% (w/w biomass). Addition of about 8% (w/w biomass) NaOH to a solvent containing 20-80% ethanol in water (v/v) and ~0.5% anthraquinone (AQ) (w/v) as a catalyst for lignin fragmentation resulted in an increase in retention of xylan in pretreatment compared to autohydrolysis (performed in EtOH/H$_2$O only).

Embodiments of the present methods include solvent solutions comprising 20-80% v/v ethanol in H$_2$O with 2% to 20% NH$_3$ (w/w biomass) and 0.5% to 8% NaOH (w/w biomass). The optimum recovery was observed for sugar cane bagasse at 40-70% EtOH in H$_2$O (v/v) and 6% NH$_3$ (w/w biomass) and 2% NaOH (w/w biomass). Increased lignin extraction with increasing EtOH in H$_2$O was observed and likely reflects the increased solubility of the lignin fragments and increased NH$_3$/NH$_4^+$ with increasing EtOH in H$_2$O owing to the decrease in solvent polarity. The higher enzymatic sugar yield and lignin extraction with NH$_3$ plus NaOH as opposed to NH$_3$ alone is likely a consequence of the higher pH in the former, resulting in a higher concentration of unprotonated NH$_3$, producing greater ammonolysis of lignin and of hemicellulose ester linkages, increased hydrolysis due to a higher concentration of OH$^-$, in the presence of NaOH in the pretreatment, and a reduced pH drop due to the hydrolysis of the hemicellulose acetyl groups.

According to the present method, the organic solvent solution comprising ammonia may optionally comprise at least one additional (inorganic) base, such as sodium hydroxide (as discussed above), sodium carbonate, potassium hydroxide, potassium carbonate, calcium hydroxide and calcium carbonate. At least one additional base may be added in an amount that is combined with ammonia to form an amount of total base that is less than about 20 wt % relative to biomass dry weight. Preferably the total one additional base plus ammonia is in an amount that is less than about 20%, or about 0%, 2%, 4%, 6%, 8%, 10%, 12%, 14%, 16%, 18 or 20% relative to dry weight of biomass.

The inorganic base could be used at various concentrations of at least from 0.5% to about 16% (wt % of dry biomass). More suitable are the concentrations from 1% to 10%. Most suitable are the concentrations between 2% to 8%.

Lignocellulosic Biomass

The lignocellulosic biomass pretreated herein includes, but is not limited to, bioenergy crops, agricultural residues, municipal solid waste, industrial solid waste, sludge from paper manufacture, yard waste, wood and forestry waste. Examples of biomass include, but are not limited to corn cobs, crop residues such as corn husks, corn stover, grasses, wheat, wheat straw, barley, barley straw, hay, rice straw, switchgrass, waste paper, sugar cane bagasse, sugar cane straw, yellow poplar, sorghum, soy, components obtained from milling of grains, trees, branches, roots, leaves, wood chips, sawdust, shrubs and bushes, vegetables, fruits, flowers and animal manure.

In one embodiment, the lignocellulosic biomass includes agricultural residues such as corn stover, wheat straw, barley straw, oat straw, rice straw, canola straw, and soybean stover; grasses such as switchgrass, miscanthus, cord grass, and reed canary grass; fiber process residues such as corn fiber, beet pulp, pulp mill fines and rejects and sugar cane bagasse; sugar cane straw and sorghum; forestry wastes such as yellow poplar, aspen wood, other hardwoods, softwood and sawdust; and post-consumer waste paper products; as well as other crops or sufficiently abundant lignocellulosic material.

In another embodiment, biomass that is useful for the invention includes biomass that has a relatively high carbohydrate content, is relatively dense, and/or is relatively easy to collect, transport, store and/or handle.

In another embodiment of the invention, biomass that is useful includes corn cobs, corn stover, sugar cane bagasse sugar cane straw, yellow poplar and switchgrass.

The lignocellulosic biomass may be derived from a single source, or can comprise a mixture derived from more than one source; for example, biomass could comprise a mixture of corn cobs and corn stover, or a mixture of stems or stalks and leaves.

In the present method, the biomass dry weight is at an initial concentration of at least about 9% up to about 80% of the weight of the biomass-solvent suspension during pretreatment. More suitably, the dry weight of biomass is at a concentration of from about 15% to about 70%, 15% to about 60%, or about 15% to about 50% of the weight of the biomass-solvent suspension. The percent of biomass in the biomass-solvent suspension is kept high to reduce the total volume of pretreatment material, decreasing the amount of solvent and reagents required and making the process more economical.

The biomass may be used directly as obtained from the source, or may be subjected to some preprocessing, for example, energy may be applied to the biomass to reduce the size, increase the exposed surface area, and/or increase the accessibility of lignin and of cellulose, hemicellulose, and/or oligosaccharides present in the biomass to organosolv pretreatment and to saccharification enzymes used, respectively, in the second and third steps of the method. Energy means useful for reducing the size, increasing the exposed surface area, and/or increasing the accessibility of the lignin, and the cellulose, hemicellulose, and/or oligosaccharides present in the biomass to the organosolv pretreatment and to saccharification enzymes include, but are not limited to, milling, crushing, grinding, shredding, chopping, disc refining, ultrasound, and microwave. This application of energy may occur before or during pretreatment, before or during saccharification, or any combination thereof.

Drying prior to pretreatment may occur as well by conventional means, such as exposure at ambient temperature to vacuum or flowing air at atmospheric pressure and or heating in an oven at atmospheric pressure or a vacuum oven.

Pretreatment Conditions

Pretreatment of biomass with an organic solvent solution comprising ammonia and one more nucleophile, under alkaline conditions, is carried out in any suitable vessel. Typically the vessel is one that can withstand pressure, has a mechanism for heating, and has a mechanism for mixing the contents. Commercially available vessels include, for example, the Zipperclave® reactor (Autoclave Engineers, Erie, Pa.), the Jaygo reactor (Jaygo Manufacturing, Inc., Mahwah, N.J.), and a steam gun reactor (described in General Methods Autoclave Engineers, Erie, Pa.). Much larger scale reactors with similar capabilities may be used. Alternatively, the biomass and organosolv solution may be combined in one vessel, then transferred to another reactor. Also biomass may be pretreated in one vessel, then further processed in another reactor such as a steam gun reactor (described in General Methods; Autoclave Engineers, Erie, Pa.).

The pretreatment reaction may be performed in any suitable vessel, such as a batch reactor or a continuous reactor. One skilled in the art will recognize that at higher temperatures (above 100° C.), a pressure vessel is required. The suitable vessel may be equipped with a means, such as impellers, for agitating the biomass-organosolv mixture. Reactor design is discussed in Lin, K.-H., and Van Ness, H. C. (in Perry, R. H. and Chilton, C. H. (eds), Chemical Engineer's Handbook, $5^{th}$ Edition (1973) Chapter 4, McGraw-Hill, N.Y.). The pretreatment reaction may be carried out either as a batch, or a continuous process.

Prior to contacting the biomass with solvent, vacuum may be applied to the vessel containing the biomass. By evacuating air from the pores of the biomass, better penetration of the solvent into the biomass may be achieved. The time period for applying vacuum and the amount of negative pressure that is applied to the biomass will depend on the type of biomass and can be determined empirically so as to achieve optimal pretreatment of the biomass (as measured by the production of fermentable sugars following saccharification).

The heating of the biomass with solvent is carried out at a temperature of from about 100° C. to about 220° C., about 150° C. to 200° C., or about 165° C. to about 195° C. The heated solution may be cooled rapidly to room temperature. In still another embodiment, the heating of the biomass is carried out at a temperature of about 180° C. Heating of the biomass-solvent suspension may occur for about 5 minutes to about 5 hours, or for about 30 minutes to about 3 hours, or more preferably from about 1 to 2 hours.

The pretreatment of biomass with the organic solvent solution and ammonia occurs under alkaline conditions at a pH that is equal to or greater than the pKa of the nucleophiles present. Under these high pH conditions, at least 50% of the nucleophiles are in their deprotonated states. Deprotonation typically increases the reactivity of the nucleophiles. The nucleophiles present, in addition to ammonia, can include alkylamines, polysulfides (hydropolysulfides) and sulfides (hydrosulfides), and thiols.

For the pretreatment methods described herein, the temperature, pH, time of pretreatment and concentration of reactants such as the organic solvent and ammonia and the additional nucleophile, biomass concentration, biomass type and biomass particle size are related; thus these variables may be adjusted as necessary for each type of biomass to optimize the pretreatment processes described herein.

Following pretreatment at elevated temperature the biomass is filtered under pressure. The filtration may either be preceded or not by cooling. Following filtration, the biomass may be washed one or more times with hydrated organic solvent at elevated or at ambient temperature. It may then either be washed with water or dried to remove the organic solvent and then saccharified. Methods for drying the biomass were described above.

To assess performance of the pretreatment, i.e., the production of readily saccharifiable carbohydrate-enriched biomass, with high retention of hemicellulose, and subsequent saccharification, separately or together, the theoretical yield of sugars derivable from the starting biomass can be determined and compared to measured yields. Pretreatment performance may be further assessed by relating how enzyme loadings affect target product yields in overall system performance.

Further Processing

Saccharification

Following pretreatment, the readily saccharifiable carbohydrate-enriched biomass comprises a mixture of organic solvent, ammonia, nucleophile, fragmented and extracted lignin and polysaccharides. Prior to further processing, ammonia, nucleophile and lignin fragments may be removed from the pretreated biomass by filtration and washing the sample with EtOH in $H_2O$ (0% to 100% EtOH v/v). The biomass may be washed with water to remove EtOH or dried resulting in carbohydrate-enriched, readily saccharifiable biomass and the concentration of glucan, xylan and acid-insoluble lignin content of said biomass may be determined using analytical means well known in the art. It is a real benefit of this invention that the pretreated biomass can be either washed with water or dried for saccharification. The readily saccharifiable carbohydrate-enriched biomass, with high retention of hemicellulose, may then be further hydrolyzed in the presence of a saccharification enzyme consortium to release oligosaccharides and/or monosaccharides in a hydrolysate.

Surfactants such as Tween 20 or Tween 80 or polyoxyethylenes such as PEG 2000, 4000 or 8000 may be added to improve the saccharification process (U.S. Pat. No. 7,354,743 B2, incorporated herein by reference). The addition of surfactant (e.g., Tween 20) to the enzymatic saccharification often enhances the rate and yield of monomeric sugar release. It is likely that the surfactant coats any residual lignin, decreasing the non-productive binding of the enzyme to the lignin. An alternative approach is to either enhance the extraction of lignin in the pretreatment or to modify the lignin chemically such that less enzyme is lost to lignin adsorption.

Saccharification enzymes and methods for biomass treatment are reviewed in Lynd, L. R., et al., (Microbiol. Mol. Biol. Rev., 66:506-577, 2002). The saccharification enzyme consortium may comprise one or more glycosidases; the glycosidases may be selected from the group consisting of cellulose-hydrolyzing glycosidases, hemicellulose-hydrolyzing glycosidases, and starch-hydrolyzing glycosidases. Other enzymes in the saccharification enzyme consortium may include peptidases, lipases, ligninases and esterases.

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223: 1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, in isolated form, such as Spezyme® CP cellulase (Genencor International, Rochester, N.Y.) and Multifect® xylanase (Genencor). In addition, saccharification enzymes may be expressed in host organisms at the biofuels plant, including using recombinant microorganisms.

One skilled in the art would know how to determine the effective amount of enzymes to use in the consortium and adjust conditions for optimal enzyme activity. One skilled in the art would also know how to optimize the classes of enzyme activities required within the consortium to obtain optimal saccharification of a given pretreatment product under the selected conditions.

Preferably the saccharification reaction is performed at or near the temperature and pH optima for the saccharification enzymes. The temperature optimum used with the saccharification enzyme consortium in the present method ranges from about 15° C. to about 100° C. In another embodiment, the temperature optimum ranges from about 20° C. to about 80° C. and most typically 45-50° C. The pH optimum can range from about 2 to about 11. In another embodiment, the pH optimum used with the saccharification enzyme consortium in the present method ranges from about 4 to about 5.5.

The saccharification can be performed for a time of about several minutes to about 120 hours, and preferably from about several minutes to about 48 hours. The time for the reaction will depend on enzyme concentration and specific activity, as well as the substrate used, its concentration (i.e., solids loading) and the environmental conditions, such as temperature and pH. One skilled in the art can readily determine optimal conditions of temperature, pH and time to be used with a particular substrate and saccharification enzyme(s) consortium.

The saccharification can be performed batch-wise or as a continuous process. The saccharification can also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using cellulases stable and more active at higher pHs and temperatures followed by hemicellulases that are active at lower pHs and temperatures.

The degree of solubilization of sugars from biomass following saccharification can be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem., 31: 426-428, 1959). Alternatively, sugars can be measured by HPLC using an appropriate column as described below.

Fermentation to Target Products:

The readily saccharifiable carbohydrate-enriched biomass, with high retention of hemicellulose, produced by the present methods may be hydrolyzed by enzymes as described above to produce fermentable sugars which then can be fermented into a target product. "Fermentation" refers to any fermentation process or any process comprising a fermentation step.

Target products include, without limitation alcohols (e.g., arabinitol, butanol, ethanol, glycerol, methanol, 1,3-propanediol, sorbitol, and xylitol); organic acids (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); ketones (e.g., acetone); amino acids (e.g., aspartic acid, glutamic acid, glycine, lysine, serine, and threonine); gases (e.g., methane, hydrogen ($H_2$), carbon dioxide ($CO_2$), and carbon monoxide (CO)).

Fermentation processes also include processes used in the consumable alcohol industry (e.g., beer and wine), dairy industry (e.g., fermented dairy products), leather industry, and tobacco industry.

Further to the above, the sugars produced from saccharifying the pretreated biomass as described herein may be used to produce in general, organic products, chemicals, fuels, commodity and specialty chemicals such as xylose, acetone, acetate, glycine, lysine, organic acids (e.g., lactic acid), 1,3-propanediol, butanediol, glycerol, ethylene glycol, furfural, polyhydroxyalkanoates, cis,cis-muconic acid, and animal feed (Lynd, L. R., Wyman, C. E., and Gerngross, T. U., Biocom. Eng., Biotechnol. Prog., 15: 777-793, 1999; and Philippidis, G. P., Cellulose bioconversion technology, in Handbook on Bioethanol: Production and Utilization, Wyman, C. E., ed., Taylor & Francis, Washington, D.C., 179-212, 1996; and Ryu, D. D. Y., and Mandels, M., Cellulases: biosynthesis and applications, Enz. Microb. Technol., 2: 91-102, 1980).

Potential coproduction of products may also be produced, such as multiple organic products from fermentable carbohydrate. Lignin-rich residues remaining after pretreatment and fermentation can be converted to lignin-derived chemicals, chemical building blocks or used for power production.

Conventional methods of fermentation and/or saccharification are known in the art including, but not limited to, saccharification, fermentation, separate hydrolysis and fermentation (SHF), simultaneous saccharification and fermentation (SSF), simultaneous saccharification and cofermentation (SSCF), hybrid hydrolysis and fermentation (HHF), and direct microbial conversion (DMC).

SHF uses separate process steps to first enzymatically hydrolyze cellulose to sugars such as glucose and xylose and then ferment the sugars to ethanol. In SSF, the enzymatic hydrolysis of cellulose and the fermentation of glucose to ethanol is combined in one step (Philippidis, G. P., supra). SSCF includes the cofermentation of multiple sugars (Sheehan, J., and Himmel, M., Bioethanol, Biotechnol. Prog., 15: 817-827, 1999). HHF includes two separate steps carried out in the same reactor but at different temperatures, i.e., high temperature enzymatic saccharification followed by SSF at a lower temperature that the fermentation strain can tolerate. DMC combines all three processes (cellulase production, cellulose hydrolysis, and fermentation) in one step (Lynd, L. R., Weimer, P. J., van Zyl, W. H., and Pretorius, I. S., Microbiol. Mol. Biol. Rev., 66: 506-577, 2002).

These processes may be used to produce target products from the carbohydrate-enriched biomass, with high retention of hemicellulose, produced by the pretreatment methods described herein.

Advantages of the Present Methods

Methods described in this invention for pretreatment of the lignocellulosic biomass using fragmentation and selective extraction of lignin at elevated temperatures under alkaline conditions in combination with low to moderate concentrations of ammonia result in significantly improved lignin fragmentation and high carbohydrate, particularly hemicellulose, retention thus providing a cost effective process to obtain carbohydrate-enriched biomass for enzymatic saccharification. Such biomass then, produces very high yields of fermentable sugars (glucose, as well as xylose) for their bioconversion to value-added chemicals and fuels.

Among the key weaknesses of current organosolv processes described in the literature are: the poor recoveries of carbohydrate, particularly xylose, following pretreatment, the requirement for separate hexose and pentose streams, the production of sugar breakdown products, the use of large amounts of solvent and high capital cost. For example, certain existing processes include use of acidic organosolv conditions which produces hydrolysates of hemicellulose and cellulose. The greater lability of the hemicellulose under acidic conditions results in the formation of breakdown products of monomeric xylose (e.g. furfural), greatly reducing the recovery of xylose (Pan et al., supra). In one version of this process (Arato, C., Pye, E. K., and Gjennestad, G., Appl. Biochem. Biotech. 121-124: 871-882, 2005), the hemicellulose is hydrolyzed under acidic conditions and the cellulose, following neutralization, is hydrolyzed enzymatically. The need to neutralize the acid prior to saccharification, the partial loss of xylose, and the processing of separate pentose and hexose streams all add to the costs of the process. Furthermore, the use of acidic conditions, requires the use of alloys in the reactors and piping that substantially add to the capital cost of the equipment.

This disclosure describes development of a highly selective process in which the lignin is selectively fragmented and extracted using inexpensive reagents and the hemicellulose and the cellulose remain together in the biomass to be later saccharified enzymatically. This process particularly allows maintaining high concentrations of the hemicellulose of the biomass. The amount of lignin extracted into the organic solvent solution is ≧75% and the xylan and glucan recoveries in the residual biomass are close to quantitative thus overcoming the weaknesses of procedures described in the literature for organosolv biomass pretreatment as described above. The high recoveries of polysaccharide, according to the methods described in this application, arise because of the use of alkaline conditions that diminish hemicellulose hydrolysis and sugar breakdown, the use of low to moderate concentrations of ammonia, that prevents polysaccharide peeling under alkaline conditions, and the high ethanol content of the organic solvent solution which reduces the hydrolysis of hemicellulose and renders insoluble xylose oligomers. In addition, the alkaline conditions used do not require the use of exotic alloys in the equipment, thereby lowering capital cost. Performing this process with little or no inorganic salt among the reactants or products (e.g., NaOH, $NaCO_3$, $CaSO_4$) results in little or no cost associated with disposal of inorganic waste material at the end. The unreacted reagent (e.g., EtOH, $NH_3$) is recyclable providing additional cost-saving benefits. Many of the processes described in the literature use large solvent to biomass ratios. In the present case, the use of alkaline conditions and the substantial fragmentation of the lignin by the added nucleophiles means that the solvent streams can accumulate high concentrations of lignin, reducing the need for large solvent volumes and at the same time reducing the loss of trace amounts of solubilized carbohydrate. Finally, the residual carbohydrate saccharifies well using enzymes, likely because of the high level of extraction of lignin fragments in the pretreatment, the effective scission of ester linkages between hemicellulose and lignin, and some lowering of the degree of polymerization of the polysaccharide. The use of organic solvent improves the wettability of the biomass and the ability of enzyme to penetrate into the pores of the substrate.

EXAMPLES

Pretreatment of Biomass to Obtain Readily Saccharifiable Carbohydate-Enriched Biomass The goal of the experimental work described below was to develop an economical pretreatment process for lignocellulose that maximized lignin extraction and sugar retention in the pretreatment and to produce a readily saccharifiable carbohydrate-enriched biomass with high retention of hemicellulose that may be further processed to obtain maximal monomeric sugar yields following enzymatic saccharification. The approach adopted was to selectively fragment and extract the lignin into a suitable solvent while retaining the sugars in the solids residue. The following experiments show the development of an organic solvent solution that combines the presence of nucleophiles like $NH_3$ for selective extraction of lignin. The combined presence of an organic solvent and low to moderate concentration of $NH_3$ and optionally an additional base selectively fragmented and dissolved the lignin components of biomass providing for the generation of pretreated biomass containing high levels of carbohydrates particularly hemicellulose.

Cane bagasse, was milled in a Wiley knife mill through a 1 mm screen prior to pretreatment.

The following abbreviations are used in the Examples: "HPLC" is High Performance Liquid Chromatography, "C" is degrees Centigrade or Celsius; "%" is percent; "wt" is weight; "w/w" is weight for weight; "mL" is milliliter; "OD" is outer diameter; "ID" is internal diameter; "h" is hour(s); "rpm" is revolution per minute; "EtOH" is ethanol; "mg/g" is milligram per gram; "g/100 mL" is gram per 100 milliliters; "N" is normal; "g" is gram; "NaOH" is sodium hydroxide; "w/v" is weight per volume; "v/v" is volume for volume; "$NH_3$" is ammonia; "mm" is millimeter; "mL/min" is milliliter per minute; "min" is minutes; "mM" is millimolar.

Materials

Sulfuric acid, ammonium hydroxide, acetic acid, acetamide, yeast extract, 2-morpholinoethanesulfonic acid (MES), potassium phosphate, glucose, xylose, tryptone, sodium chloride, citric acid, monomethyl and dimethylamine were obtained from Sigma-Aldrich (St. Louis, Mo.). Spezyme CP and Multifect CX12L were from Genecor (Genencor International, Palo Alto, Calif.) and Novozyme 188 was from Novozyme (Bagsvaerd, Denmark).

Example 1

Effective Ethanol Concentration

The purpose of this Example was to examine the effect of the concentration of solvent (e.g., ethanol) in water on the recovery of carbohydrate and on the solubilization/extraction of lignin in the absence of pH control. Bagasse (0.2 g, 95.78% dry matter) was suspended in 1.56 mL of an EtOH/water solution containing various concentrations (from 0 to 80%) of EtOH. The suspensions were loaded into type 316 stainless steel tubing (¼ inches ID, ⅜ inches OD, 4 inches long) capped by Swagelock fittings (Penn Fluid System Technologies, Huntingdon Valley, Pa.). These were placed in a fluidized sand bath (Techne Model SBS-4, Techne Inc., Burlington, N.J.) and heated at 180° C. for 2 h and cooled rapidly by plunging into a water bath at room temperature. The samples were removed from the tubes and filtered by centrifugation at 14,000 rpm using Spin-X filters (Costar, Corning Inc., Corning N.Y.) at room temperature in a table top centrifuge (Spectrifuge 16M, Labnet International Inc., Edison, N.J.) to remove the dissolved lignin. The retentate of each sample was washed (4x) with 0.5 mL of EtOH/$H_2O$ using the same EtOH concentration as used in the 180° C. treatment (0-80% EtOH in $H_2O$). The samples were then allowed to air dry at room temperature (to ~92% dry matter) and the glucan, xylan and acid-insoluble lignin contents of the residues determined using the National Renewable Energy Laboratory (NREL) procedure (Determination of Structural Carbohydrates and Lignin in Biomass-Version 2006, Amie Sluiter et al., available from the NREL website).

Subsequent Enzymatic Saccharification

The air-dried sample prepared above was suspended in 50 mM citrate buffer, pH 4.6 at a ~14% solids loading. The saccharification enzymes, e.g. Spezyme CP, Multifect CX12L and Novozyme 188 were added at concentrations of 6:3:6 mg/g cellulose, respectively. Also added were 1% (w/v) Tween 20 and 0.01% (w/v) $NaN_3$, the latter to prevent microbial growth. Samples (~0.4 mL) were placed in screw cap vials containing two 5 mm glass beads and incubated at 46° C. on a rotary shaker run at 250 rpm. Aliquots were removed for analysis at 4 h and at every 24 h interval from the start and diluted 41.25-fold with 0.01 $NH_2SO_4$. The samples were then filtered through Spin-X filters and the filtrates were analyzed by HPLC (Agilent series 1100/1200, Agilent Technologies, Wilmington, Del.). A BioRad HPX-87H Aminex column (Bio-Rad Laboratories, Hercules Calif. 94547 was used to fractionate the released sugars using 0.01 $NH_2SO_4$ as the mobile phase at a flow rate of 0.6 mL/min. The column was maintained at 60° C. A differential refractive index detector was used to detect the eluted sugars and was maintained at 55° C. The retention times for glucose, xylose and arabinose were 9.05, 9.72 and 10.63 min, respectively). Table 1A outlines the percentages of glucan and xylan recovery and the percent change in acid insoluble (AI) lignin content after pretreatments at EtOH concentrations of 0%-80%. Concentration of Bagasse was (0.2 g/1.56 mM) variable concentrations of EtOH were used at 180° C. for 2 h.

TABLE 1A

Glucan and xylan recovery following pretreatment according to Example 1

| Pretreatment (% EtOH in water) | % Glucan recovery in residue | % Xylan recovery in residue | AI lignin content % change |
|---|---|---|---|
| 0 | 83.0% | 29.0% | +27.6% |
| 20 | 88.7% | 30.8% | +15.2% |
| 40 | 86.0% | 57.6% | −10% |
| 60 | 91.9% | 87.4% | −25.6% |
| 80 | 88.6% | 91.1% | −28.8% |

Results shown in Table 1A indicate that lignin extraction increased with increasing EtOH content presumably because the solubility of lignin increased with increasing EtOH concentration. However, the amount of lignin extracted remained modest even at high ethanol concentrations.

Hemicellulose hydrolysis and the solubility of xylose oligomers decreases with increasing EtOH, increasing the recovery of xylan and xylose oligomers in the residue. The amount of acetate liberated by the pretreatment also decreased with increasing EtOH content, consistent with decreasing auto hydrolysis of the biomass at increasing EtOH concentration.

Table 1B shows the glucose and xylose yields after 96 h of enzymatic saccharification following pretreatment at different EtOH concentrations. The saccharification of cellulose increased when the concentration of EtOH in pretreatment was increased from 0 to 20%, but then declined with higher pretreatment concentrations of EtOH. A likely decrease in partial hydrolysis of lignin and cellulose (increase in degree of polymerization, of cellulose which lowered the glucose yield on subsequent saccharification—Table 1B) was observed at concentrations of more than 20% EtOH.

TABLE 1B

Monomeric glucose and xylose yields following enzymatic saccharification for 96 h, pretreated as described in Example 1

| % EtOH in water (v/v) | Glucose monomer saccharification only (% theoretical yield) | Xylose monomer saccharification only (% theoretical yield) | Glucose monomer overall yield (% theoretical yield) | Xylose monomer overall yield (% theoretical yield) |
|---|---|---|---|---|
| 0 | 38.43 | 34.98 | 31.86 | 10.16 |
| 20 | 44.48 | 45.52 | 39.46 | 14.01 |
| 40 | 29.62 | 38.55 | 25.45 | 22.23 |
| 60 | 16.81 | 24.64 | 15.45 | 21.52 |
| 80 | 6.8 | 7.22 | 6.02 | 7.01 |

The overall monomeric sugar recoveries (Table 1B), particularly of xylose, were quite poor at the lower EtOH concentrations. At low EtOH concentration in the pretreatment, the acidic conditions, produced at high temperatures by hydrolysis of the acetyl groups of the hemicellulose, hydrolyze the hemicellulose. The solubilized xylose and some glucose is lost in the filtration and washes that follow the pretreatment. At higher EtOH concentrations there is less partial hydrolysis of the cellulose, hemicellulose and lignin which lowers the saccharification yield. The behavior at the low and high ethanol concentrations together produce low overall yields of monomeric glucose and xylose.

Example 2

Effect of Alkaline Organic Solvent Solution Pretreatment on Lignin Extraction

The purpose of this Example was to examine the effect of raising the pH on organic solvent solution pretreatment at different EtOH in $H_2O$ ratios on carbohydrate retention and lignin extraction and on monomeric sugar during subsequent enzymatic saccharification. Given that autohydrolysis lowers the pH, hydrolyzes xylan, and promotes the loss of xylose, the pH of the pretreatment was elevated by the addition of NaOH. The effect of higher pH on xylose recovery is demonstrated below. Sugar cane bagasse (0.25 g, 95.78% dry matter) was suspended in 1.75 mL of a solvent containing EtOH (20-80% in water) and 8% NaOH (w/w biomass) plus 1 mg anthraquinone (AQ, a catalyst for lignin fragmentation). The initial pH of this solution was ~13.7. The suspensions were loaded into type 316 stainless steel tubing, capped, treated at 168° C. for 140 min and cooled in room-temperature water. The samples were removed from the pressure vessels, filtered, washed, air-dried and analyzed all as described above in Example 1. The glucan, xylan, arabinan contents and change in lignin content following pretreatment are shown in Table 2A.

Subsequent enzymatic saccharification was carried out as described in Example 1 except that the Spezyme:Multifect:Novozymes 188 ratio was 12:6:1.2 mg/g dry solids in the presence of 1% Tween 20 (w/v). Table 2B shows the monomeric sugar yields after 96 h of enzymatic saccharification of biomass previously pretreated at the different EtOH concentrations.

TABLE 2A

Glucan, xylan and arabinan yields following pretreatment according to Example 2

| Pretreatment % EtOH in water | % Glucan recovery in residue | % Xylan recovery in residue | % Arabinan recovery in residue | Al lignin content % change |
|---|---|---|---|---|
| 20 | 77.5% | 74.6% | 51.3% | −48 |
| 45 | 84.0% | 85.1% | 68.0% | −64 |
| 60 | 83.6% | 85.5% | 76.0% | −63 |
| 70 | 81.3% | 84.2% | 75.8% | −65 |
| 80 | 80.0% | 84.2% | 86.6% | −50 |

TABLE 2B

Monomeric glucose and xylose yields following enzymatic saccharification for 96 h, pretreated as described in Example 2

| % EtOH in $H_2O$ | Glucose monomer saccharification only (% theoretical yield) | Xylan monomer saccharification only (% theoretical yield) | Glucose monomer overall yield (% theoretical yield) | Xylose monomer overall yield (% theoretical yield) |
|---|---|---|---|---|
| 20 | 57.72 | 68.56 | 44.7 | 51.2 |
| 45 | 58.19 | 73.08 | 48.9 | 62.2 |
| 60 | 49.51 | 64.56 | 41.4 | 55.2 |
| 70 | 24.48 | 39.06 | 19.9 | 32.9 |
| 80 | 0.63 | 1.33 | 0.5 | 1.1 |

As can be seen in Tables 2A and 2B, the alkaline conditions of this experiment substantially increased the retention of xylan in the pretreatment compared to the autohydrolysis experiments of Example 1. This effect was most pronounced at low EtOH concentrations. The NaOH prevented the solution from becoming acidic (final pH ~10.7) and therefore protected the hemicellulose from acid-catalyzed hydrolysis. In addition, significantly more lignin was extracted, presumably through base catalyzed fractionation of the lignin. The overall monomeric sugar yields following saccharification were substantially higher than those observed in Example 1. The higher sugar recovery and the greater lignin extraction in the pretreatment, increased the yields of the subsequent enzymatic saccharification. The xylose and glucose saccharification yields peaked at ~45% EtOH as a consequence of two opposing processes, i.e., the increasing extraction of lignin at higher EtOH which tends to increase the sugar yields, and the decreasing partial hydrolysis of hemicellulose and of lignin as the EtOH concentration is further increased. It is likely that the formation of quinone methides, which could repolymerize or react with sugars, and "peeling' and alkaline scission reactions of polysaccharide all together contribute to limit the overall sugar yields.

Example 3

Further Increase of Saccharification Yield Following Pretreatment in the Presence of Ammonia The purpose of the Example was to study the effect of the presence of ammonia in the organic solvent solution on the carbohydrate yield and lignin content following pretreatment and monomeric sugar yield following saccharification. While the xylan recovery was substantially improved by the increase in pH, there were still substantial sugar losses in the alkaline pretreatment process outlined in Example 2. These losses are likely due to "peeling", i.e., stripping sugars from the reducing end of the polysaccharide chains. It is also possible that the lignin, while more effectively hydrolyzed under alkaline conditions as compared to autohydrolysis, forms quinone methides which are capable of repolymerization and of reaction with reducing sugars. Consequently, the effect of addition of $NH_3$ to the organic solvent solution was examined with the intent of blocking both of these phenomena.

Sugar cane bagasse (0.375 g, 95.78% dry matter) was suspended in 1.125 mL of solvent containing various percentages of EtOH (0%-70% in water). In addition, the solvent contained 6% $NH_3$ and 2% NaOH (w/w biomass). The initial pH of this solution was 13.2 and increased to pH 14.0 with increasing EtOH concentration. These conditions were compared to a similar bagasse sample suspended in 70% EtOH in $H_2O$ (v/v) containing 8% $NH_3$ (w/w biomass) alone where the initial pH was 12.2. The suspensions were loaded into type 316 stainless steel pressure vessels (3/16 inches ID, 1/4 inches OD, 4 inches long), capped and treated as described above in Example 1, except that solids loading was higher and the samples were heated at 168° C. for 140 min.

Subsequent enzymatic saccharification was carried out as described in Example 1 except that the Spezyme:Multifect: Novozymes 188 ratio was 6.68:3.34:1.67 mg/g dry solids in the presence of 1% Tween 20 (w/v). The solids loading was 14 wt %.

Table 3A summarizes the pretreatment results at the various EtOH concentrations. Table 3B summarize saccharification following pretreatment at different EtOH concentrations in the presence of 6% $NH_3$ plus 2% NaOH (w/w biomass) after 96 h.

TABLE 3A

Glucan, xylan and arabinan recovery following pretreatment outlined in Example 3

| Pretreatment % EtOH in water | % Glucan recovery in residue | % Xylan recovery in residue | % Arabinan recovery in residue | Al lignin content % change | Initial pH |
|---|---|---|---|---|---|
| 0 | 90.1% | 92.5% | 69.7% | −17% | 13.22 |
| 20% | 91.4% | 97.1% | 74.6% | −25% | 13.46 |
| 40% | 95.6% | 102% | 79.7% | −37% | 13.72 |
| 70% | 97.8% | 107% | 92.4% | −47% | 14.0 |
| 70% (8% $NH_3$ only) | 87.9% | 94.5% | 73.3% | −22% | 12.12 |

TABLE 3B

Monomeric glucose and xylose yields following enzymatic saccharification for 96 h, pretreated as described in Example 3

| % EtOH in water | Glucose monomer saccharification only (% theoretical yield) | Xylose monomer saccharification only (% theoretical yield) | Glucose monomer overall (% theoretical yield) | Xylose monomer overall (% theoretical yield) | Arabinose monomer overall (% theoretical yield) |
|---|---|---|---|---|---|
| 0 | 69.7 | 57.8 | 62.8 | 53.5 | 58.9 |
| 20 | 77.1 | 63.9 | 70.5 | 62 | 66.4 |
| 40 | 76.8 | 67.6 | 73.4 | 69 | 69 |
| 70 | 73.6 | 65.4 | 71.9 | 69.8 | 76 |
| 70 (8% $NH_3$ only) | 68.8 | 58.1 | 60.5 | 54.9 | 57.6 |

It is clear from the results outlined in Tables 3A and 3B that the carbohydrate recoveries in the residue are substantially increased in the alkaline ammonia pretreatment as compared to NaOH alone (Example 2). In addition, the low concentration $NH_3$ addition produces a substantial increase in both the monomeric glucose and xylose yields upon enzymatic saccharification of samples pretreated at the higher concentration EtOH in $H_2O$ pretreatment conditions. These results are consistent with a role for $NH_3$ to either block "peeling" reactions or to lower the concentration of quinone methides or both. The presence of a low concentration of NaOH in the presence of $NH_3$ significantly increases the efficacy of the pretreatment, probably because, at the higher pH in the presence of NaOH, more of the $NH_3$ is in the deprotonated form.

Example 4

Effect of Addition of Methylamine and Elemental Sulfur to Organic Solvent Solution Pretreatment Containing Ammonia Pretreatment with ammonia was examined in the presence of the added nucleophiles, methylamine and elemental sulfur, which under the alkaline conditions of the pretreatment disproportionates to form polysulfides and sulfide. Pretreatment was performed as in Example 3 except that the bagasse contained 1% elemental sulfur (w/w biomass) and was suspended in 70% EtOH in $H_2O$ (v/v) plus either 14% MA (methylamine), 7% $NH_3$+7% MA, 10% $NH_3$+4% MA, or 14% $NH_3$ (all w/w biomass). The samples were heated at 187° C. for 1 h in the pressure vessels and then rapidly cooled to room temperature in water bath. The residue was filtered, washed and dried as previously described. Enzymatic saccharification was performed as in Example 5, but in the presence and absence of 0.5% PEG 2000 (w/w biomass).

TABLE 4

The yield of monomeric sugars following treatment described in Example 11

| Sample 70% EtOH in H$_2$O (v/v) + 1% S (w/w biomass) + additives (w/w biomass) | % Glucan recovery in solids | % Xylan recovery in solids | Monomeric glucose (% of theoretical yield) without PEG | Monomeric xylose (% of theoretical yield) without PEG | Monomeric glucose (% of theoretical yield) with PEG | Monomeric xylose (% of theoretical yield) with PEG |
|---|---|---|---|---|---|---|
| 14% MA | 96.8 | 102.3 | 83.3 | 74.6 | 85.8 | 75.8 |
| 7% NH$_3$ + 7% MA | 90.80 | 96.98 | 79.5 | 68.2 | 82.9 | 71.1 |
| 10% NH$_3$ + 4% MA | 91.61 | 97.35 | 76.2 | 66.4 | 80.8 | 68.7 |
| 14% NH$_3$ | 95.24 | 100.41 | 66.71 | 59.5 | 74.3 | 63.9 |

As indicated in Table 9, replacement of ammonia with methylamine does not have an impact on the glucan and xylan recovery upon pretreatment. The saccharification yields for both monomeric glucose and xylose, however, increase progressively the more extensive the replacement of ammonia with methylamine (Table 4). The differences between the saccharification runs with and without PEG 2000 are for the most part only a few percent. An economic analysis of the overall process is required to determine whether the higher yields of sugar production upon either the replacement of ammonia with methylamine in the pretreatment or upon addition of PEG 2000 in the saccharification, offset the added cost of MA or PEG.

What is claimed is:

1. A method for producing fermentable sugars comprising:
   (a) providing lignocellulosic biomass comprising lignin, cellulose and hemicellulose;
   (b) suspending the biomass of (a) in an organic solvent solution comprising water, ammonia in an amount of about 2% to about 20% relative to weight of dry biomass and one or more nucleophile, whereby a biomass-solvent suspension is formed under alkaline conditions;
   (c) heating the biomass-solvent suspension to a temperature of about 100-220° C. for about 5 minutes to about 5 hours whereby lignin is fragmented and is dissolved in the suspension;
   (d) filtering free liquid under pressure after heating the suspension in (c) whereby the dissolved lignin is removed and whereby carbohydrate-enriched biomass with high retention of hemicellulose is produced;
   (e) optionally washing the carbohydrate-enriched biomass of (d) with an organic solvent solution producing a solvent-washed carbohydrate-enriched biomass;
   (f) removing solvent from the carbohydrate-enriched biomass of (e), or of (d) when (e) is omitted;
   wherein a readily saccharifiable carbohydrate-enriched biomass is produced; and
   (g) contacting the readily saccharifiable carbohydrate-enriched biomass of (f) with an enzyme consortium, whereby fermentable sugars are produced.

2. The method of claim 1 wherein removing solvent is by washing with water or drying.

3. The method of claim 1 wherein step (e) is repeated one or more times.

4. The method of claim 1 further comprising fermenting the sugars to produce a target product.

5. The method of claim 4 wherein the target product is selected from the group consisting of alcohols, organic acids, amino acids and gases.

6. The method of claim 5 wherein the target product is selected from the group consisting of ethanol, butanol, or 1,3-propanediol.

7. The method of claim 1, wherein said one or more nucleophile is selected from the group consisting of NaOH, one or more alkylamines, sulfide, hydrosulfide, polysulfide, hydropolysulfide, thiol reagents, and combinations thereof.

8. The method of claim 7 wherein the one or more alkylamines is selected from the group consisting of R—NH$_2$, R$_2$—NH, R$_3$N, (H$_2$N—R—NH$_2$), (H$_2$N—R(NH$_2$)$_2$), (HO—R—NH$_2$), ((HO)$_2$—R—NH$_2$), (HO—R—(NH$_2$)$_2$), (HS—R—NH$_2$), ((HS)$_2$—R—NH$_2$), (HS—R—(NH$_2$)$_2$) and (H$_2$N—R(OH)(SH) and combinations thereof, wherein R is independently a monovalent, divalent or trivalent 1-6 carbon alkane, alkene or alkyne, linear, cyclic or branched.

9. The method of claim 8 wherein R is independently methyl, ethyl, propyl or butyl.

10. The method of claim 8 wherein the alkylamine is methylamine.

11. The method of claim 8 wherein the alkylamine is at a concentration of less than about 20% relative to dry weight of biomass.

12. The method of claim 1 wherein the solvent solution to biomass in step (b) has a weight ratio of about 10 to 1 to 0.5 to 1.

13. The method of claim 1, wherein the heated suspension of step (c) is cooled to room temperature before filtering in step (d).

14. The method of claim 1 wherein the biomass is selected from the group consisting of switchgrass, waste paper, sludge from paper manufacture, corn fiber, corn cobs, corn husks, corn stover, grasses, wheat, wheat straw, hay, barley, barley straw, rice straw, sugar cane bagasse, sugar cane straw, yellow poplar, sorghum, soy, components obtained from processing of grains, trees, branches, roots, leaves, wood chips, sawdust, shrubs and bushes, vegetables, fruits, flowers, animal manure and combinations thereof.

15. The method of claim 1 wherein the organic solvent solution of (b) further comprises one or more additional components selected from the group consisting of alkali or alkaline earth hydroxides or carbonates, ammonia, thiols, sulfides, hydrosulfides, polysulfides, hydropolysulfides, and combinations thereof.

16. The method of claim 1 wherein the organic solvent solution of (b) and any ammonia or other unreacted components are recyclable.

17. The method of claim 1 wherein the organic solvent solution of (b) and the organic solvent solution of (e) comprise a solvent independently selected from the group consisting of alcohols, diols and aprotic solvents.

18. The method of claim 17 wherein the organic solvent solution comprises a solvent selected from the group consisting of methanol, ethanol, propanol, butanol, pentanol and hexanol, isomers thereof, and diols thereof.

19. The method of claim 18 wherein the organic solvent solution comprises from about 40% to about 70% ethanol in water.

* * * * *